(12) United States Patent
Yadav et al.

(10) Patent No.: US 10,882,819 B2
(45) Date of Patent: Jan. 5, 2021

(54) SYNTHESIS OF NOVEL INTERMEDIATE(S) FOR PREPARING RIVASTIGMINE

(71) Applicant: Cadila Pharmaceuticals Ltd., Gujarat (IN)

(72) Inventors: Jhillu Singh Yadav, Kadi (IN);
Gyanchander Eppa, Kalol (IN);
Pranav Rameshbhai Vachharajani, Gujarat (IN); Nutan Bharatbhai Vekariya, Gujarat (IN); Chetan Umeshbhai Bhavsar, Gujarat (IN); Rajiv Indravadan Modi, Gujarat (IN); Bakulesh Mafatlal Khamar, Gujarat (IN)

(73) Assignee: Cadila Corporate Campus, Gujarat (IN)

( * ) Notice: Subject to any disclaimer, the term of this patent is extended or adjusted under 35 U.S.C. 154(b) by 0 days.

(21) Appl. No.: 16/582,303

(22) Filed: Sep. 25, 2019

(65) Prior Publication Data
US 2020/0095195 A1 Mar. 26, 2020

(30) Foreign Application Priority Data
Sep. 26, 2018 (IN) .............................. 201821036203

(51) Int. Cl.
*C07C 269/04* (2006.01)
*C07C 271/44* (2006.01)

(52) U.S. Cl.
CPC .......... *C07C 269/04* (2013.01); *C07C 271/44* (2013.01)

(58) Field of Classification Search
CPC .............................. C07C 269/04; C07C 271/44
See application file for complete search history.

(56) References Cited

U.S. PATENT DOCUMENTS

| | | | |
|---|---|---|---|
| 4,948,807 A | 8/1990 | Rosin et al. | |
| 5,602,176 A | 2/1997 | Enz | |
| 7,385,076 B2 * | 6/2008 | Patel | C07C 269/06 560/136 |
| 7,683,205 B2 * | 3/2010 | Deshpande | C07C 213/08 560/136 |
| 7,767,843 B2 * | 8/2010 | Wang | C07C 269/04 560/132 |
| 7,884,121 B2 * | 2/2011 | Raheem | C07D 233/54 514/399 |
| 8,420,846 B2 * | 4/2013 | Dubey | C07C 213/00 558/48 |

FOREIGN PATENT DOCUMENTS

| | | |
|---|---|---|
| CN | 103304447 B | 9/2015 |
| CN | 103193679 B | 4/2016 |
| EP | 1697313 B1 | 9/2015 |
| IN | 2981/CHE/2010 A | 7/2012 |
| IN | 2722/CHE/2010 A | 3/2013 |
| IN | 1520/MUM/2012 A | 3/2019 |
| WO | 2004037771 A1 | 5/2004 |
| WO | 2005058804 A1 | 6/2005 |

OTHER PUBLICATIONS

Han et al., "Chemoenzymatic Synthesis of Rivastigmine via Dynamic Kinetic Resolution as a Key Step", vol. 75, No. 9, J. Org. Chem., 2010 (pp. 3105-3108).

Mangas-Sanchez et al., "Chemoenzymatic Synthesis of Rivastigmine Based on Lipase-Catalyzed Processes" vol. 74, No. 15, J. Org. Chem., 2009 (pp. 5304-5310).

* cited by examiner

*Primary Examiner* — Yate' K Cutliff
(74) *Attorney, Agent, or Firm* — Burns & Levinson LLP; Jerry Cohen

(57) ABSTRACT

The present invention relates to novel intermediate(s), which are useful for the preparation of Rivastigmine compound of formula (I) and its pharmaceutically acceptable salts. The present invention further relates to the processes for the preparation of such novel intermediate(s) and preparation of Rivastigmine using such novel intermediate(s).

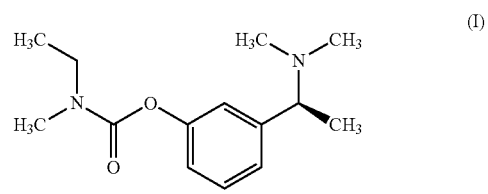

8 Claims, No Drawings

SYNTHESIS OF NOVEL INTERMEDIATE(S) FOR PREPARING RIVASTIGMINE

CROSS REFERENCE TO RELATED APPLICATION

This application claims the benefit of and priority to the Indian Application Number 201821036203, filed on Sep. 26, 2018, which is incorporated by reference herein in its entirety.

FIELD OF THE INVENTION

The present invention relates to novel intermediate(s) useful for the preparation of Rivastigmine or its pharmaceutically acceptable salts. The present invention further relates to processes for the preparation of the said novel intermediate(s).

BACKGROUND OF THE INVENTION

Rivastigmine which is chemically known as (S)—N-Ethyl-3-[(1-dimethylamino)ethyl]-N-methylphenylcarbamate or Ethylmethylcarbamic acid 3-[(1S)-1-(dimethylamino)ethyl]phenyl ester is represented by a compound of formula (I):

Rivastigmine hydrogen tartrate is a reversible cholinesterase inhibitor and is useful in the treatment of Alzheimer's disease.

U.S. Pat. No. 4,948,807 discloses the compound N-ethyl, N-methyl-3-[1(dimethylamino) ethyl]phenyl carbamate and pharmacologically acceptable salts thereof with a process for preparation as depicted in scheme-1. US '807 describes the amidation of 3-[1-(dimethylamino)ethyl]hydroxyphenyl with an isocyanate or its carbamoyl halide. This patent does not mention the conversion of racemic mixture into its optically active enantiomers.

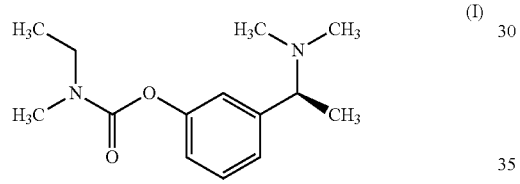

Scheme-1

U.S. Pat. No. 5,602,176 discloses the enantiomeric form i.e. Rivastigmine which is chemically named as (S)—N-ethyl-3-[(1-dimethylamino)ethyl]-N-methyl-phenyl-carbamate] in free base or acid addition salt. US '176 discloses the preparation of desired enantiomer by resolution of racemic N-ethyl-3-[(1-dimethylamino)ethyl]-N-methyl-phenyl-carbamate with di-O,O'-p-toluyl tartatic acid monohydrate (DPTTA) followed by repeated crystallizations in methanol/water.

WO 2004037771 A1 describes a process for preparation of (S)—[N-ethyl-3-[(1-dimethylamino)ethyl]-N-methyl-phenyl-carbamate, wherein optically active m-hydroxyphenylethyl dimethyl amine is obtained by resolution of corresponding recemic amine using (S)-(+)-camphor-10-sulphonic acid. The main drawback of this process are low yield obtained during the resolution of (S)-3-[(1-dimethylamino)ethyl]phenol and repeated crystallization required for getting the optically pure compound.

WO 2005058804 A1 describes a process for preparation of rivastigmine by stereo selective reduction of ketone as depicted in scheme-2.

Scheme-2

The reported advantage of said process is the formation of desired (S)-isomer and avoiding the formation of undesired (R)-isomer by stereo selective reduction. However, the process involves stereo-selective reduction, which requires the use of chiral coordinated transition metal complex for catalyzing the hydrogenation. These chiral coordinated transition metal complexes are very expensive and thereby make process uneconomical on industrial scale.

EP 1697313 discloses the process for preparation of Rivastigmine by converting a phenylcarbamate ketone to the aminoalkyl phenylcarbamate in presence of sodium cynoborohydride followed by addition of DPTTA and repeated crystallization to obtain Rivastigmine. Use of Sodium cyanoborohydride makes the aforesaid process not viable at industrial scale. In alternate process disclosed in EP '313 for preparing Rivastigmine involves in use of corrosive reagent such as phosphorus tribromide, which is environmental unfriendly.

IN 2722/CHE/2010 discloses the process for preparation of Rivastigmine involves the stereo-selective reduction of 3-acetylphenyl ethyl (methyl) carbamate in presence of {(S)-Xyl-Binap-RuCl$_2$—(S)-Daipen, base and hydrogen gas pressure to obtain (R)-3-(1-hydroxyethyl)phenyl ethyl (methyl) carbamate. The aforesaid mentioned process involves the use of chiral coordinated transition metal complexes, which are expensive and thereby makes process uneconomical on industrial scale.

IN 2981/CHE/2010 discloses the enzymatic reduction process for reduction of ethyl methyl carbamic acid 3-acetyl phenyl ester to ethyl-methyl carbamic acid-(1S-hydroxyethyl)phenyl ester using ketoreducase enzyme. J. Org. Chem. 2009, 74, 5304-5310 & J. Org. Chem. 2010, 75, 3105-3108 disclose the enzymatic resolution process of 3-(1-Hydroxyethyl)phenyl ethyl (methyl) carbamate using Novozym-435 enzyme to give enantiomerically enriched product. However, in aforesaid processes, the enzymatic resolution reaction cycle is longer and special techniques are required for enzyme screening and process.

IN 1520/MUM/2012 describes the chiral reduction of 3-methoxy acetophenone or Ethyl-methyl-carbamic acid 3-acetyl-phenyl ester in presence of (+)-B-Chlorodiisopinocampheylborane (DIP chloride) in organic solvent to obtain corresponding chiral 1-(3-methoxy phenyl)ethanol or Ethyl-methyl-carbamic acid 3-(1-hydroxy-ethyl)-phenyl ester, which further convert into Rivastigmine. The aforementioned process requires higher mole amount of chiral catalysts i.e. DIP chloride per mole of substrate, which renders the process industrially uneconomical. In addition to expensive, DIP chloride is both corrosive and moisture sensitive, causing burns if allowed to come in contact with the skin.

CN 103193679 B, CN 103304447 B also discloses the use expensive chiral catalysts for conversion of N-ethyl-N-methyl carbamic acid-3-acetyl phenyl ester to a Rivastigmine chiral intermediate compound of (R)—N-ethyl-N-methyl carbamic acid-3-(1-hydroxyethyl) phenyl ester.

Although each of the above patents and/or reference represents an attempt to improve the efficiency of obtaining Rivastigmine or its pharmaceutically acceptable salts with improved yield and purity, there still exists a need for a cost-effective process for large scale production of Rivastigmine or its pharmaceutically acceptable salts, which provides improved yield with higher chemical and optical purity.

OBJECT OF THE INVENTION

The main object of the present invention is to provide novel intermediate(s) useful for the preparation of Rivastigmine or its pharmaceutical acceptable salts.

Another object of the present invention is to provide a process for the preparation of the said novel intermediate(s).

Another object of the present invention is to obtain the desired optically active intermediate(s) with high optical purity. This leads to improved yield of the desired product with considerably less amount of the undesired isomer.

Another object of the present invention is to provide a cost-effective process for large scale production of (S)—N-ethyl-N-methyl-3-[(1-dimethylamino)ethyl] phenyl carbamate (Rivastigmine) of formula I or its pharmaceutically acceptable salts.

SUMMARY OF THE INVENTION

In one embodiment, the present invention provides a process for the preparation of compound of formula (V),

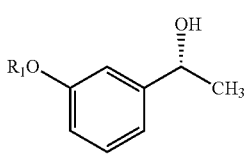

(V)

wherein $R_1$ represent $C_1$-$C_3$ alkyl or

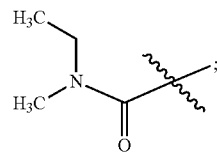

comprising the steps of:
a) reacting a compound of formula (II) with phthalic anhydride to obtain a compound of formula (III);

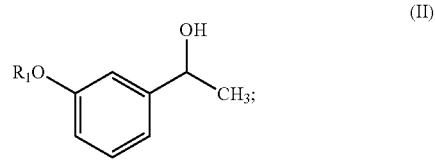

(II)

(III)

b) reacting the compound of formula (III) with a chiral resolving agent of formula (VI) to obtain a compound of formula (IV);

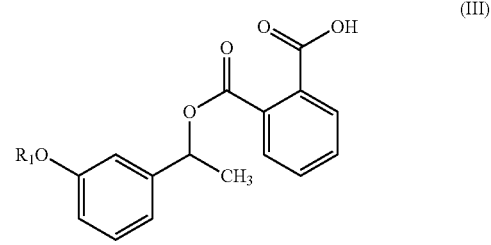

(VI)

(IV)

wherein * is a stereogenic center; $R_2$, $R_3$ and $R_4$ are selected from hydrogen, $C_{1-4}$ alkyl, $C_{6-10}$ aryl and $C_{7-12}$ alkylaryl which are optionally substituted with one or more methyl or methoxy, wherein $R_3$ and $R_4$ are different; and c) converting the compound of formula (IV) into the compound of formula (V).

In another embodiment, the present invention provides a process for the preparation of Rivastigmine of formula (I) or its pharmaceutically acceptable salts comprising the steps of:

a) reacting a compound of formula (IIa) with phthalic anhydride to obtain a compound of formula (IIIa);

(IIa)
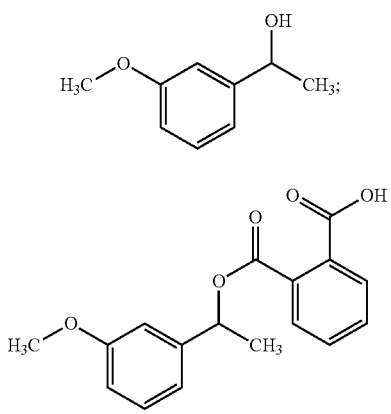

(IIIa)

b) reacting the compound of formula (IIIa) with (R)-1-phenylethylamine to obtain a compound of formula (IVa);

(IVa)
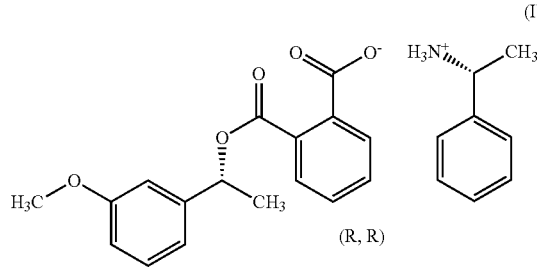

c) converting the compound of formula (IVa) into the compound of formula (Va); and (Va)
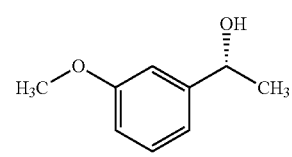

d) converting the compound of formula (Va) to Rivastigmine of formula (I) or its pharmaceutically acceptable salt.

In another embodiment, the present invention provides a process for the preparation of Rivastigmine of formula (I) or its pharmaceutically acceptable salts comprising the steps of:

a) reacting a compound of formula (IIb) with phthalic anhydride to obtain a compound of formula (IIIb);

(IIb)
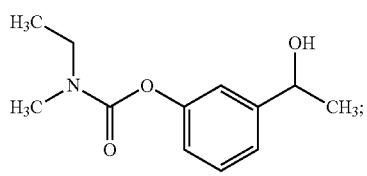

(IIIb)

b) reacting the compound of formula (IIIb) with (R)-1-phenylethylamine to obtain a compound of formula (IVb);

(IVb)

c) converting the compound of formula (IVb) into the compound of formula (Vb); and (Vb)
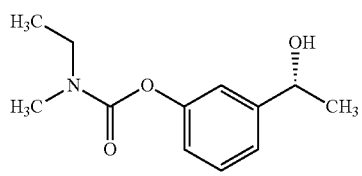

d) converting the compound of formula (Vb) to Rivastigmine of formula (I) or its pharmaceutically acceptable salt.

In another embodiment, the present invention provides a compound of formula (III), (III)
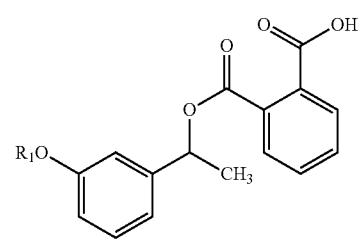

wherein $R_1$ is as defined herein above.

In another embodiment, the present invention provides a compound of formula (IV):

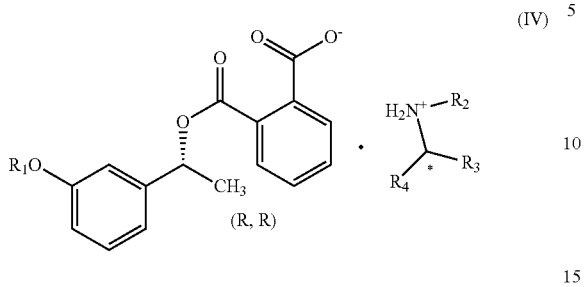

wherein *, $R_1$, $R_2$, $R_3$ and $R_4$ is same as defined above.

In another embodiment, the present invention relates to the use of compound of formula (III) for the preparation of Rivastigmine of formula (I) or its pharmaceutically acceptable salt.

In another embodiment, the present invention relates to the use of compound of formula (IV) for the preparation of Rivastigmine of formula (I) or its pharmaceutically acceptable salt.

In another embodiment, the present invention provides a process for the preparation of Rivastigmine compound of formula (I) or its pharmaceutically acceptable salts thereof by converting the compound of formula (V) into Rivastigmine by any method known in the art.

DETAILED DESCRIPTION OF INVENTION

The embodiments herein and various features thereof are explained in greater depth with reference to the non-limiting embodiments that are detailed in following description.

In one embodiment, the present invention provides a process for the preparation of compound of formula (V) as shown in Scheme-3:

Scheme-3

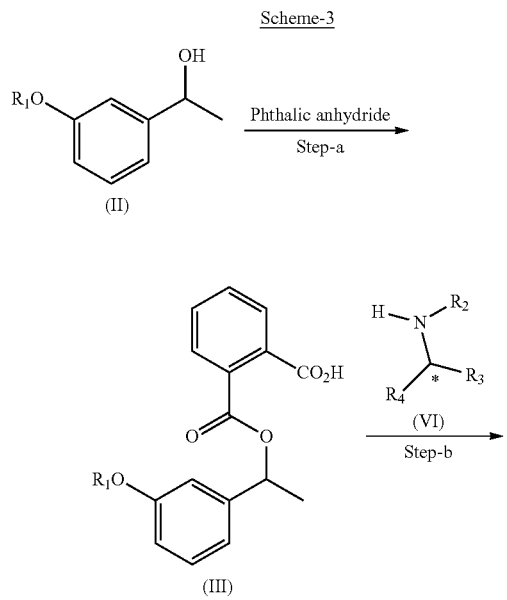

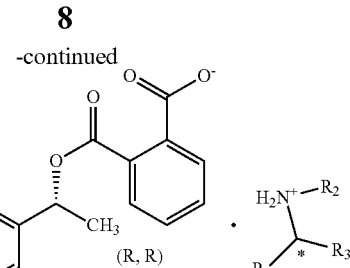

wherein $R_1$ represent $C_1$-$C_3$ alkyl or

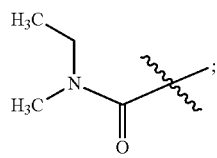

$C_1$-$C_3$ alkyl represents methyl, ethyl, propyl or isopropyl; * is a stereogenic center; $R_2$, $R_3$ and $R_4$ are selected from hydrogen, $C_{1-4}$ alkyl, $C_{6-10}$ aryl, or $C_{7-12}$ alkylaryl which are optionally substituted with one or more methyl or methoxy; wherein $R_3$ and $R_4$ are different.

The step (a) of aforesaid process can be carried out in presence of suitable base and suitable organic solvent optionally in the presence of catalyst.

The suitable base of step (a) can be selected from a group comprising of inorganic base or organic base. In particular, the inorganic base comprises carbonates like potassium carbonate, sodium carbonate; bicarbonates like sodium bicarbonate, potassium bicarbonate; hydroxides like sodium hydroxide, potassium hydroxide or Lithium hydroxide. In particular, the organic base comprises N,N-dimethylamine, N-ethyl-N-methylamine, triethylamine, N,N-dimethylbenzylamine, N,N-diethylbenzylamine, N-methylmorpholine, dimetylaminopyridine, pyridine and the like.

The catalyst of step (a) can be selected from 4-dimethylaminopyridine (DMAP), N,N-diisopropylethylamine (DIPEA) and the like.

The organic solvent of the step (a) can be selected from a group comprising of one or more halogenated hydrocarbons, nitriles, amides, ethers and the like. The suitable halogenated hydrocarbons include, but are not limited to, methylene chloride, ethylene chloride, chloroform, and the like, and mixtures thereof. The suitable nitriles include, but are not limited to, acetonitrile, propionitrile, benzonitrile, and the like, and mixtures thereof. The suitable amides include, but are not limited to, dimethyl formamide, dimethyl acetamide, N-methyl pyrrolidinone, and the like, and mixtures thereof. The suitable ethers include, but are not limited to, tetrahydrofuran, dimethyl ether, diisopropyl ether, methyl tertiary butyl ether, 1,4-dioxane, and the like, and mixtures thereof.

The reaction of step (a) can be carried out at any suitable range of temperature generally at 20° C.-140° C., preferably at 20° C.-40° C. over a period of about 1 to 5 hours, preferably for 1 to 2 hours.

The step (b) of aforesaid process can be carried out in the presence of chiral resolving agent of formula (VI) in suitable organic solvent optionally in the presence of inorganic base.

The chiral resolving agent of formula (VI) of the step (b) can be selected from a group comprising of 1-phenylethyl-amine, 1-Phenylpropyl amine, α-Methyl-1-naphthalenem-ethyl amine, N-benzyl-1-phenylethylamine, N,N-bis[α-methyl benzyl]amine, 1-(3-methoxyphenyl)ethylamine, 1-(3,4-dimethoxy-phenyl)ethyl amine, α-phenyl-β-(p-tolyl) ethylamine, 1-methyl-3-phenylpropylamine Preferably, chiral resolving agent of formula (VI) can be selected from group consisting of (R)-1-phenylethylamine, (R)-(+)-1-Phenylpropylamine and (R)-(+)-α-Methyl-1-naphthalenemethylamine.

Generally, the resolution is carried out in the presence of 0.4 to 0.7 moles equivalent of chiral resolving agent of formula (VI) per mole of a compound of formula (III).

The organic solvent of the step (b) can be selected from a group comprising of one or more halogenated hydrocarbons, alcohol, water, ester, ethers and the like. The suitable halogenated hydrocarbons include, but are not limited to, methylene chloride, ethylene chloride, chloroform, and the like, and mixtures thereof. The suitable alcohols includes, but are not limited to, methanol, isopropanol, ethanol, and the like, and mixtures thereof. The suitable esters includes, but are not limited to, ethyl acetate, propyl acetate, isopropyl acetate, and the like, and mixtures thereof. The suitable ethers include, but are not limited to, tetrahydrofuran, dimethyl ether, diisopropyl ether, methyl tertiary butyl ether, 1,4-dioxane, and the like, and mixtures thereof.

The suitable inorganic base of step (b) can be selected from a group comprises carbonates like potassium carbonate, sodium carbonate; bicarbonates like sodium bicarbonate, potassium bicarbonate; hydroxides like sodium hydroxide, potassium hydroxide or Lithium hydroxide.

The reaction of step (b) can be carried out at any suitable range of temperature generally at 20° C.-100° C., preferably at 25° C.-80° C. over a period of about 10 minutes to 5 hours, preferably for 15 minutes to 2 hours.

The reaction step (c) can be preceded first by desaltification of the compound of formula (IV) in the presence of acid and followed by ester hydrolysis in the presence of base to obtain the compound of formula (V).

In general, the desaltification of the compound of formula (IV) can be carried out in the presence of suitable acid and solvent. Suitable acids are selected from the group consisting of organic carboxylic acids, sulfonic acids, and inorganic acids. The inorganic acid may be hydrochloric acid, hydrobromic acid, sulfuric acid, pivalic acid or phosphoric acid, preferably hydrochloric acid. The organic carboxylic acid may be formic acid, oxalic acid, acetic acid, trimethyl acetic acid or trifluoroacetic acid, preferably acetic acid. The sulfonic acid may be methanesulphonic acid or p-toluene sulfonic acid.

The desaltification reaction of step (c) can be carried out at any suitable range of temperature generally at 20° C.-80° C., preferably at 30° C.-60° C. over a period of about 0.5 to 6 hours, preferably for 0.5 to 2 hours.

The ester hydrolysis of the step (c) can be carried out in the presence of suitable inorganic base selected from a group comprises carbonates like potassium carbonate, sodium carbonate; bicarbonates like sodium bicarbonate, potassium bicarbonate; hydroxides like sodium hydroxide, potassium hydroxide or lithium hydroxide.

The ester hydrolysis of step (c) can be carried out at any suitable range of temperature generally at 20° C.-100° C., preferably at 30° C.-90° C. over a period of about 0.5 to 6 hours, preferably for 0.5 to 2 hours.

The suitable solvent for the desaltification and ester hydrolysis for the step (c) can be same or different and selected from the group comprising of alcohols such as methanol, ethanol, propanol, isopropanol and butanol and the like; chlorinated hydrocarbons such as methylene chloride, chloroform and the like; ethers such as diisopropyl ether, methyl tert-butyl ether, dioxane, tetrahydrofuran and the like; esters such as ethyl acetate, isopropyl acetate and the like; ketone solvent such as methyl isobutyl ketone, acetone and the like; polar aprotic solvents such as dimethylformamide, dimethyl sulfoxide, N-methylpyrrolidone, and water or mixture thereof.

In another embodiment, the present invention provides a preparation of 3-methoxyphenyl intermediate of formula (Va) as depicted in scheme-4 by following the reaction conditions as mentioned herein above:

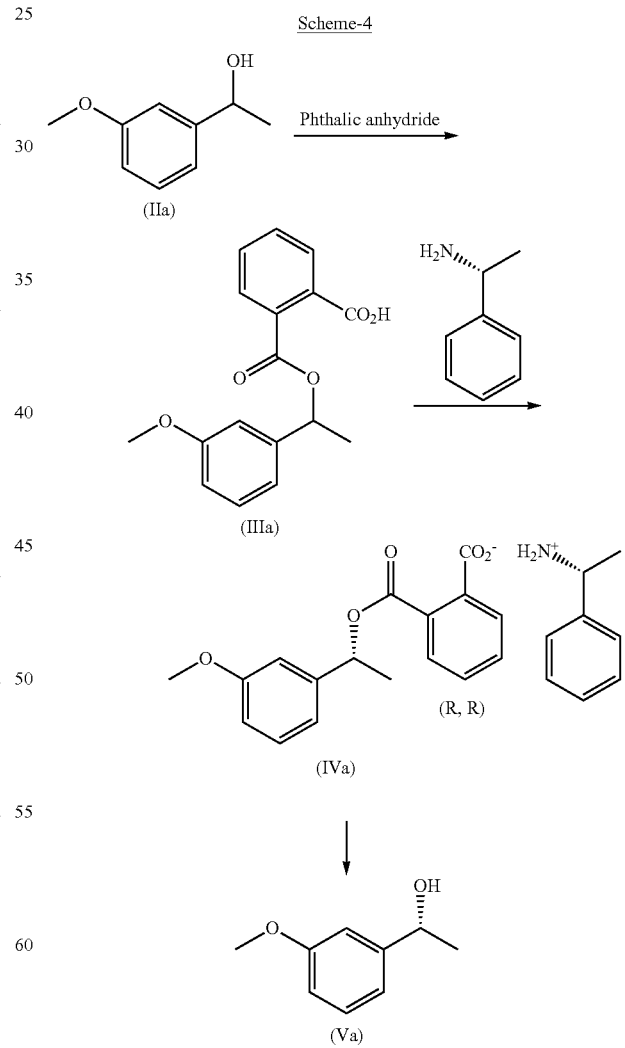

Scheme-4

In another embodiment, the present invention provides a preparation of phenyl carbamate intermediate of formula (Vb) as depicted in scheme-4 by following the reaction conditions as mentioned herein above:

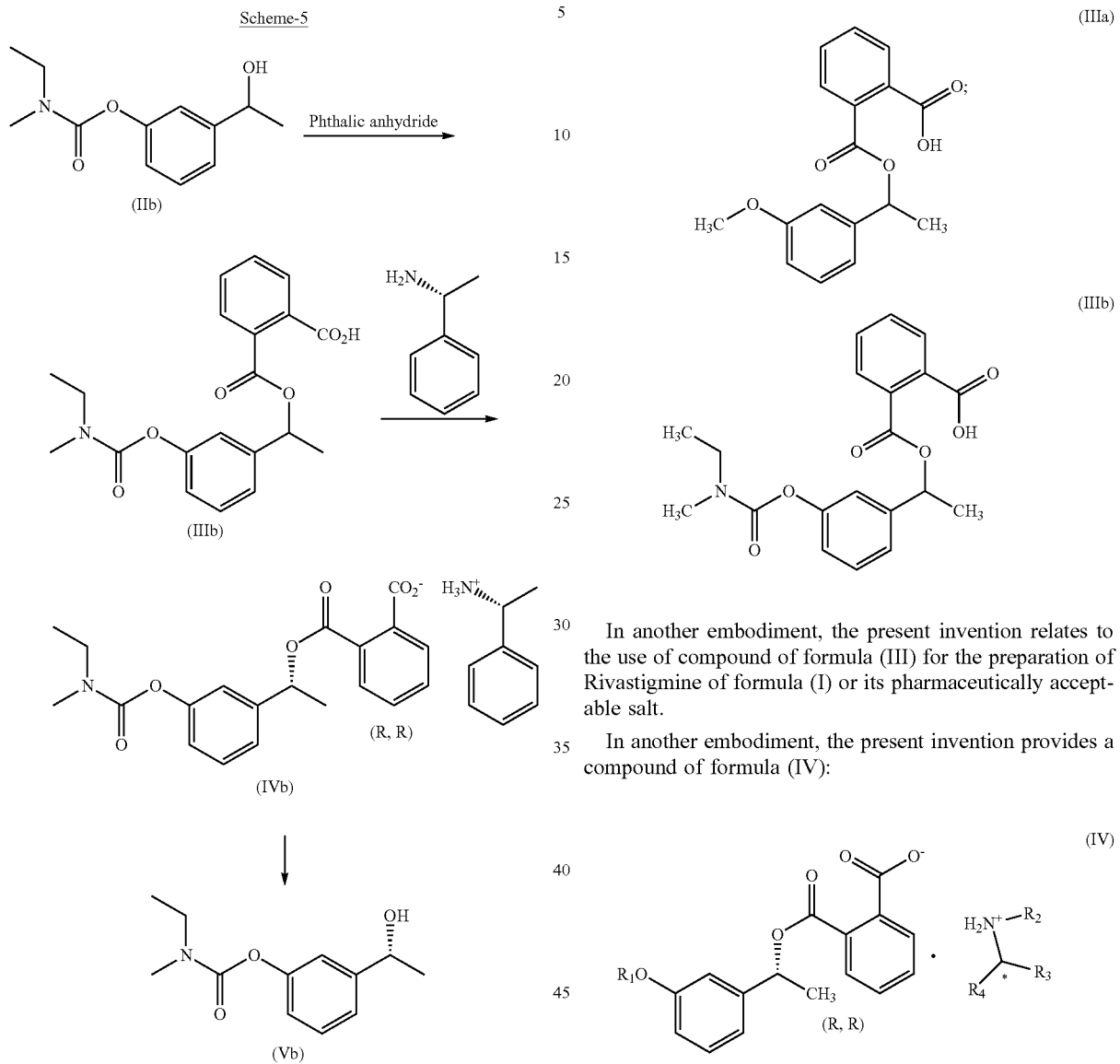

In another embodiment, the present invention provides a compound of formula (III):

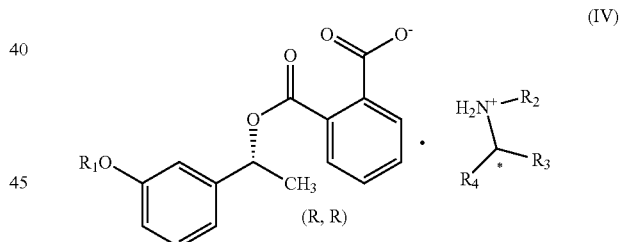

and its salts.
wherein, R is as defined herein above.

In particular, the present invention provides a compound of formula (IIIa) or (IIIb):

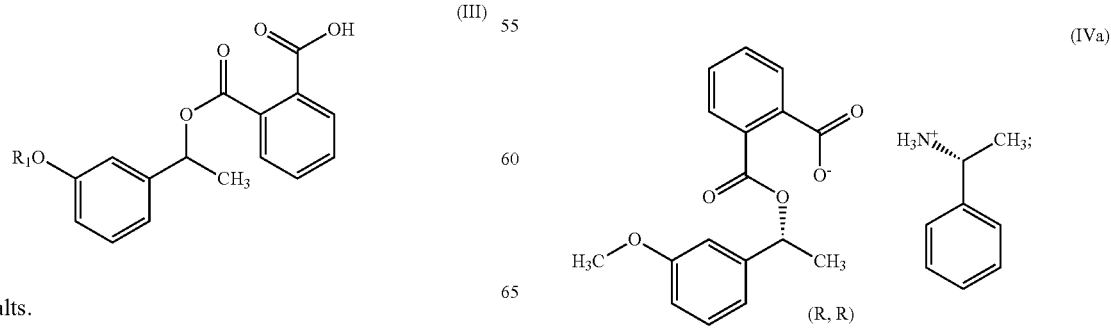

In another embodiment, the present invention relates to the use of compound of formula (III) for the preparation of Rivastigmine of formula (I) or its pharmaceutically acceptable salt.

In another embodiment, the present invention provides a compound of formula (IV):

wherein $R_1$, $R_2$, $R_3$ and $R_4$ is same as defined above.

In particular, the present invention provides a compound of formula (IVa) or (IVb):

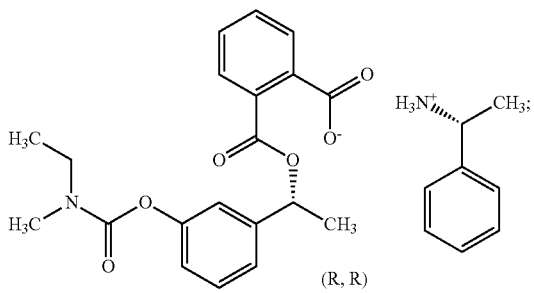

(IVb)

In another embodiment, the present invention relates to the use of compound of formula (IV) for the preparation of Rivastigmine of formula (I) or its pharmaceutically acceptable salt.

In another embodiment, the compound of formula (V) can be converted into Rivastigmine or its pharmaceutically acceptable salts by any suitable method or a method known in the art.

The obtained Rivastigmine optionally can be converted into its pharmaceutically acceptable salt, preferably tartrate salt by any method known in the art.

The process details of the invention are provided in the examples given below, which are provided by way of illustration only and therefore should not be construed to limit the scope of invention. Reasonable variations of the described procedures/processes are intended to be within the scope of the present invention. While particular aspects of the present application have been illustrated and described, it would be obvious to those skilled in the art that various other changes and modifications can be made without departing from the spirit and scope of the invention.

EXAMPLE(S)

Example-1: Preparation of 3-Methoxy Acetophenone

To a 1 lit. RB flask, acetone (200 ml), 3-Hydroxyacetophenone (100 g) and anhydrous potassium carbonate (121.8 g) were added and stirred for 10 min. To the above reaction mixture, added dimethyl sulphate (101.9 gm) drop wise for about 60 min followed by heating to about 45° C. and stirred reaction mass for 1 hour. After completion of reaction, the reaction mixture was quenched by charging of Demineralised (DM) water (800 ml). Layers were separated, aqueous layer was extracted with methylene dichloride (MDC) (200 ml) and combined organic layers were dried over anhydrous sodium sulphate and distilled out MDC to obtain 110 g 3-Methoxy acetophenone (Yield: 99.73%).

Example-2: Preparation of 1-(3-Methoxy-phenyl)-ethanol

To a 1 lit. RB flask, MDC (315 ml) and sodium borohydride (23.54 g) were added and stirred for 10 min. To the above reaction mixture added solution of 3-methoxy acetophenone (105 g) in methanol (105 ml) drop wise for about 60 min and stirred reaction mass for 5 hour. After completion of reaction, the reaction mixture was quenched by charging of DM water (420 ml). Layers were separated, aqueous layer was extracted with MDC (250 ml) and combined organic layers were washed with DM water (420 ml). The collected organic layer dried over anhydrous sodium sulphate and distilled out MDC to get 100 g of 1-(3-Methoxy-phenyl)-ethanol (Yield: 94.30% & Purity by HPLC: 99.59%).

Example-3: Preparation of Phthalic Acid mono-[1-(3-methoxy-phenyl)-ethyl]ester (Compound of Formula IIIa)

To a 3 lit. RB flask, MDC (400 ml), 1-(3-Methoxy-phenyl)-ethanol (80 g), dimethyl amino pyridine (6.42 g) and triethyl amine (111.68 g) were added. To the above reaction mixture phthalic anhydride (93.4 g) was added lot wise at 20-25° C. and stirred the reaction mass for 1 hour. After completion of reaction, the reaction mixture was quenched by charging of DM water (400 ml). Layers were separated, aqueous layer was extracted with MDC (200 ml) and combined organic layers were washed with diluted HCl (240 ml) and saturated brine (240 ml). The combined organic layer was dried over anhydrous sodium sulphate and distilled out MDC. Cyclohexane (160 ml) was added to the obtained residue and stirred the reaction mass for 1 hour at 5-10° C. Filtered the obtained solid followed by washing with chilled cyclohexane (40 ml) to obtain the 146 g of Phthalic acid mono-[1-(3-methoxy-phenyl)-ethyl]ester (Yield: 92.50 & Purity by HPLC: 99.45%).

$^1$H NMR (400 MHz, CDCl$_3$): δ 1.56 (d, J=7.2 Hz, 3H), δ 3.68 (s, 3H), δ 6.03 (q, J=6.4 Hz, 1H), δ 6.70-6.73 (m, 1H), δ 6.86-6.92 (m, 2H), δ 7.17 (t, 1H), δ 7.45-7.52 (m, 2H), δ 7.60-7.62 (m, 1H), δ 7.79-7.81 (m, 1H), δ 10.68 (s, broad, 1H) (D$_2$O Exchangeable).

Example-4: Preparation of Phthalic Acid mono-[1-(3-methoxy-phenyl)-ethyl]ester (R)-1-phenylethylamine Salt (Compound of Formula IVa)

To a 2 lit. RB flask, DM water (980 ml) and phthalic acid mono-[1-(3-methoxy-phenyl)-ethyl]ester (140 g) were added. To the above reaction mixture added drop wise an aqueous solution of potassium hydroxide (13.07 g in 140 ml of DM water) at 50° C. To the above reaction mixture, (R)-1-phenylethylamine (33.89 g) was added drop wise at 55-60° C. and stirred the reaction mass for 60 min at 55-60° C. The reaction mixture cooled at 40-45° C. Filter the obtained solid, washed with DM water (140 ml) and dried in vacuum oven at 50° C. to obtain 94.7 g of phthalic acid mono-[1-(3-methoxy-phenyl)-ethyl] ester (R)-1-phenylethylamine salt (Yield: 45%, Purity by HPLC: 99.91% & Chiral purity of R-isomer by HPLC: 99.79%).

$^1$H NMR (400 MHz, DMSO): δ 1.44 (d, J=6.8 Hz, 3H), δ 1.52 (d, J=6.8 Hz, 3H), 3.6 (s, broad, 3H), 3.74 (s, 3H), δ 4.28 (q, J=6.4 Hz, 1H), δ 5.91 (q, J=6.4 Hz, 1H), δ 6.82-6.85 (m, 1H), δ 6.97-7.00 (m, 2H), δ 7.24-7.48 (m, 9H), δ 7.66 (d, 1H).

Example-5: Preparation of (1R)-1-(3-Methoxy-phenyl)ethanol (Compound of Formula Va)

To a 2 lit. RB flask, ethyl acetate (960 ml), Phthalic acid mono-[1-(3-methoxy-phenyl)-ethyl] ester (R)-1-phenylethylamine salt (80 g) and dil. HCl solution (1200 ml) were added and stirred the reaction mass for 30 min. Layers were separated, organic layer washed with dil. HCl (900 ml) and distilled out ethyl acetate. To the obtained residue, an aq. solution of sodium hydroxide (37.86 g in DM water 320 ml) was added and heated the reaction mixture up to 90° C. with stirring for 60 min. The reaction mass cooled at 25-30° C.

and extracted by ethyl acetate (800 ml). The remaining aqueous layer was again extracted by ethyl acetate (400 ml), combined the organic layers and dried over sodium sulphate and distilled out ethyl acetate to obtain 28 g of (1R)-1-(3-Methoxy-phenyl) ethanol (Yield: 96.95%, Purity by HPLC: 99.57% & Chiral purity of R-isomer by HPLC: 99.69%).

$^1$H NMR (400 MHz, DMSO): δ 1.39 (d, 3H, J=6.4 Hz), δ 3.76 (s, 3H), δ 4.77 (q, 1H, J=6.4 Hz), δ 5.24 (s, 1H), δ 6.79-6.82 (m, 1H), δ 6.95-7.00 (m, 2H), δ 7.25 (t, 1H); Specific rotation [α]=+28.96° (c=0.9% in MeOH at 25° C.).

Example-6: Preparation of (1S)-[1-(3-Methoxy-phenyl)-ethyl]-dimethyl-amine

To a 500 ml. RB flask, MDC (200 ml), (1R)-1-(3-Methoxy-phenyl)-ethanol (20 g), triethylamine (26.59 g) were added and cooled the reaction mass 0 to 5° C. To above reaction mixture were added methane sulfonyl chloride (21.07 g) drop wise and stirred the reaction mass for 10 min. Purged DMA gas through the reaction mass for 30 min at 25-30° C. After completion of reaction, adjusted the pH 1 to 2 by dilute HCl. Layer were separated and aqueous layer was washed with MDC (20 ml). Collected aqueous layer, basify with 1:1 NaOH & extracted the compound in MDC. Collected MDC layer, dried over anhydrous $Na_2SO_4$ and evaporated to dryness to obtained 15.5 g of (1S)-[1-(3-Methoxy-phenyl)-ethyl]-dimethyl-amine (Yield: 65.84%, HPLC: 99.11%).

Example-7: Preparation of (1S)-3-(1-Dimethylamino-ethyl)-phenol

To a 250 ml. RB flask, (1S)-[1-(3-Methoxy-phenyl)-ethyl]-dimethyl-amine (12 g), 47% aqueous HBr (60 ml) were added and stirred the reaction mass for 8-10 hours at 110° C. After completion of reaction, cooled to room temperature, added DM water (36 ml) and adjusted the pH about 10-12 by 50% KOH. Extracted the compound in ethyl acetate, collected ethyl acetate layer, dried over anhydrous $Na_2SO_4$ and evaporated to dryness to obtained residue mass. Added 5% ethyl acetate in n-heptane in the residue, stirred for 2 hours and filtered the solid to get 8.2 g of (1S)-3-(1-Dimethylamino-ethyl)-phenol (Yield: 74%, HPLC: 98.86%).

Example-8: Preparation of Rivastigmine Base

To a 100 ml. RB flask, MDC (5 ml), and NaH (0.36 g) were added. To the above reaction mixture, a solution of (1S)-3-(1-Dimethylamino-ethyl)-phenol (1.0 g) in MDC (15 ml) was added drop wise at 20-25° C. for about 5 min and followed by added drop wise N-Ethyl N-methyl carbamoyl chloride (0.88 g) at 20-25° C. for about 5 min. Heated the reaction mass to reflux for 4 to 5 hours and cooled to room temperature. Added DM water (5 ml) followed by adjusted the pH 1 to 2 by dil. HCl. Layers were separated and MDC layer was extracted with DM water (5 ml×2). Collected and combined all aqueous layers, basify the pH 12 to 13 with 25% KOH. Extracted the compound in EtOAc (5 ml) and evaporated to dryness to obtained 1.18 g of Rivastigmine base (Yield: 77.8%, HPLC: 91.42%, Chiral HPLC: 98.09%).

Example-9: Preparation of Rivastigmine Tartrate

To a 250 ml. RB flask, Rivastigmine base (2.5 g), acetone (87.5 ml) and L-(+)-tartaric acid (1.5 g) were added. Heated the reaction mass at 60° C. for 1 hour and gradually cooled to room temperature. Filtered the reaction mass through hyflow bed and washed with acetone (12 ml). Evaporated half of the acetone volume and stirred at room temperature for 1 hour. Filtered the solid, washed with acetone and dried under vacuum to obtained 2.5 g of Rivastigmine Tartrate (Yield: 62.6%, HPLC: 99.48%, Chiral HPLC: 99.56%).

Example-10: Preparation of 3-Acetylphenyl ethyl(methyl)carbamate

To a 500 mL RB flask, acetone (100 ml), 3-Hydroxyacetophenone (10 g), Dimethyl amino pyrimidine (DMAP) (0.89 g) and triethyl amine (30.5 g) were added and stirred for 10 min. N-ethyl-N-methyl carbamoyl chloride (11.7 gm) was added to the reaction mass drop wise in about 30 min with stirring and heated to about 60-65° C. for 1 hour. After completion of reaction, the reaction mixture was filtered followed by washing with acetone (20 ml). The solvent was distilled off under vacuum at 45-50° C. The obtained reaction mass was then cooled to 25-30° C. MDC (50 ml) was added to the reaction mass and organic layer was washed with 1.5 M HCl (50 ml) and DM Water (50 ml). The combined organic layers were dried over anhydrous sodium sulphate and distilled out MDC to obtain 16.25 g 3-Acetylphenyl ethyl(methyl)carbamate (Yield: 100%; Purity by HPLC: 98.39%).

Example-11: Preparation of 3-(1-Hydroxyethyl)phenyl ethyl(methyl)carbamate

To a 250 ml RB flask, MDC (48 ml) and sodium borohydride (3.0 g) were added and stirred for 10 min at 15-20° C. 3-acetylphenyl ethyl (methyl) carbamate (16 g) in methanol (16 ml) was added to the reaction mass drop wise in about 30 min and stirred the reaction mass for 2 hour. The reaction mixture was quenched by charging of DM water (80 ml). Layers were separated and organic layer washed with brine solution (60 ml). The obtained organic layer was dried over anhydrous sodium sulphate and distilled out MDC to obtain 13.2 g of 3-(1-Hydroxyethyl) phenyl ethyl (methyl) carbamate (Yield: 81.78%; Purity by HPLC: 94.58%).

Example-12: Preparation of Phthalic Acid Mono-{1-[3-(ethyl-methyl-cabomoyloxy)-phenyl]-ethyl}ester (Compound of Formula IIIb)

To a 250 ml RB flask, MDC (33 ml), 3-(1-Hydroxyethyl) phenyl ethyl (methyl) carbamate (11 g), Dimethyl amino pyridine (0.6 g) and triethyl amine (10.47 g) were added. Phthalic anhydride (8.75 g) was added to reaction mass lot wise at 15-20° C. and stirred for 1 hour. The reaction mixture was quenched by charging of DM water (55 ml). Layers were separated and aqueous layer was extracted with MDC (33 ml). The obtained organic layers were combined and washed with dil. HCl (55 ml) and saturated brine (55 ml). The combined organic layer dried over anhydrous sodium sulphate and distilled out MDC to obtain 18.2 g of Phthalic acid mono-{1-[3-(ethyl-methyl-cabomoyloxy)-phenyl]-ethyl} ester (Yield: 100%; Purity by HPLC: 97.61%).

$^1$H NMR (400 MHz, CDCl$_3$): δ 1.29 (t, 3H), δ 1.64 (d, J=2.4 Hz, 3H), δ 3.07 (s, 3H), δ 3.49 (q, J=7.2 Hz, 2H), δ 7.06 (s, 1H), δ 7.29 (d, J=6 Hz, 1H), δ 7.38 (m, 2H), δ 6.15 (q, J=6.4 Hz, 1H), δ 7.52-7.55 (m, 2H), δ 7.70-7.72 (m, 1H), δ 7.78-7.80 (m, 1H), δ 8.06 (s, 1H); ESI (MS)=370.19 (M−H)$^+$.

Example-13: Preparation of Phthalic Acid mono-{1-[3-(ethyl-methyl-cabomoyloxy)-phenyl]-ethyl}ester (R)-1-phenylethylamine Salt (Compound of Formula IVb)

To a 250 ml RB flask, ethyl acetate (52 ml) and Phthalic acid mono-{1-[3-(ethyl-methyl-cabomoyloxy)-phenyl]-ethyl}ester (17.3 g) were added. (R)-1-phenylethylamine (3.1 g) at 55-60° C. was added to the reaction mass drop wise, stirred the reaction mass for 4 hour at 55-60° C. and distilled out ethyl acetate. To the obtained residue, methyl tert-butyl ether (52 ml) was added. The obtained reaction mass was heated at 55-60° C. for 15 min. The reaction mixture was cooled at 25-30° C. and stirred for 60 min. The obtained solid mass was filtered and washed with methyl tert-butyl ether (17 ml) and dried in vacuum oven at 50° C. to obtain 8.1 g of Phthalic acid mono-{1-[3-(ethyl-methyl-cabomoyloxy)-phenyl]-ethyl}ester (R)-1-phenylethyl amine salt (Yield: 70.6%; Purity by HPLC: 97.94%).

$^1$H NMR (400 MHz, CDCl$_3$): δ 1.23 (m, 3H), δ 1.42 (d, J=6.8 Hz, 3H), δ 1.52 (d, J=6.4 Hz, 3H), δ 3.03 (d, J=27.6 Hz, 3H), δ 3.36-3.46 (m, 2H), δ 4.13 (q, J=6.8 Hz, 1H), δ 5.96 (q, J=6.4 Hz, 1H), δ 6.98-7.64 (m, 13H), δ 8.15 (s, broad, 3H); Specific rotation [α]=−23.74° (c=0.9% in MeOH at 25° C.) ESI (MS)=493.57 (M+H)$^+$.

Example-14: Preparation of (+)-(R)-3-(1-Hydroxyethyl) phenylethyl (methyl) carbamate (Compound of Formula Vb)

To a 250 ml RB flask, ethyl acetate (20 ml), Phthalic acid mono-{1-[3-(ethyl-methyl-cabomoyloxy)-phenyl]-ethyl}ester (R)-1-phenylethylamine salt (4 g) and 1.5 M HCl solution (40 ml) were added and stirred the reaction mass for 30 min. Layers were separated, organic layer was washed with 1.5M HCl (40 ml) and ethyl acetate was distilled off from the reaction mass. To the obtained residue, a solution of sodium hydroxide (1.62 g in 16 ml DM water) was added and heated the reaction mixture up to 70° C. for 30 min. The reaction mass was cooled at 25-30° C. and extracted by ethyl acetate (20 ml). Layers were separated and an aqueous layer was extracted with ethyl acetate (20 ml) and combined organic layers dried over sodium sulphate and distilled out ethyl acetate to obtain 1.72 g of (+)-(R)-3-(1-Hydroxyethyl) phenylethyl(methyl)carbamate (Yield: 94.9%; Purity by HPLC: 96.12%).

$^1$H NMR (400 MHz, CDCl$_3$): δ 1.18-1.24 (m, 3H), δ 1.45 (d, J=6.4 Hz, 3H), δ 2.90 (s, broad, 1H), δ 3.07 (d, J=37.6 Hz, 3H), δ 3.4 (q, J=7.2 Hz, 1H), δ 3.48 (q, J=6.8 Hz, 1H), δ 4.82 (q, J=6.4 Hz, 1H), δ 6.98-7.32 (m, 4H); Specific rotation [α]=+21.77° (c=0.9% in MeOH at 25° C.); ESI (MS): 206.09 (M−OH).

Example-15: Preparation of Ethyl-methyl-carbamic Acid 3-(1-dimethylamino-ethyl)-phenyl ester (Rivastigmine Base)

To a 100 ml RB flask, MDC (23 ml), ethyl-methyl-carbamic acid 3-(1-hydroxy-ethyl)-phenyl ester (2.24 g) and triethylamine (2.78 ml) were added and cooled the reaction mass −10 to 0° C. To the above reaction mixture, added methane sulfonyl chloride (1.1 ml) drop wise and stirred for 10 min. Purged DMA gas through the reaction mixture at 25-30° C. for 30 min followed by adjusted the pH 1 to 2 by conc. HCl. Layers were separated, organic layer was extracted with DM water. Combined the aqueous layers, basify with 1:1 NaOH and extracted with ethyl acetate. Ethyl acetate was dried over anhydrous Na$_2$SO$_4$ and distilled out ethyl acetate to obtained 2.15 g of Rivastigmine base (Yield: 97%, HPLC: 96.94%, Chiral HPLC: 89.76%).

Example-16: Preparation of Phthalic Acid mono-[1-(3-methoxy-phenyl)-ethyl]ester (R)-(+)-α-Methyl-1-naphthalenemethylamine Salt To a 500 ml RB flask, DM water (140 ml) and Phthalic acid mono-[1-(3-methoxy-phenyl)-ethyl]ester (20 g) were added. To the above reaction mixture, added drop wise a solution of KOH (2.24 g) in DM water (40 ml) at 65-70° C. To the above reaction mixture was added drop wise (R)-(+)-α-Methyl-1-naphthalenemethylamine (6.27 g) at 65-70° C. Stirred the reaction mass for 60 min at 65-70° C., cooled at 25-30° C. and stirred for 60 min. Filtered the obtained solid followed by washing with DM water (60 ml) and dried in vacuum oven at 50° C. to get 12 g of Phthalic acid mono-[1-(3-methoxy-phenyl)-ethyl] ester (R)-(+)-α-Methyl-1-naphthalenemethyl amine salt (Yield: 76.5%; HPLC: 99.86%, Chiral Purity by HPLC: 95.77% (R-isomer).

1H NMR (400 MHz, DMSO): δ 1.51-1.53 (d, 3H), δ 1.54-1.55 (d, 3H), δ 3.74 (s, 3H), δ 5.13-5.17 (q, 1H), δ 5.89-5.93 (q, 1H), δ 6.82-6.85 (m, 1H), δ 6.98-7.00 (m, 2H), δ 7.23-7.27 (m, 1H), δ 7.38-7.47 (m, 3H), δ 7.52-7.69 (m, 3H), δ 7.77-7.78 (d, 1H), δ 7.88-7.90 (d, 1H), δ 7.96-7.98 (d, 1H), δ 8.13-8.15 (d, 1H), δ 3.45 (s, broad, 3H).

Example-17: Preparation of (1R)-1-(3-Methoxy-phenyl) ethanol

To a 250 ml RB flask, ethyl acetate (42 ml), Pthalic acid mono-[1-(3-methoxy-phenyl)-ethyl] ester (R)-(+)-α-Methyl-1-naphthalenemethylamine salt (6 g) and dil. HCl solution (60 ml) were added and stirred for 30 min. Separated the organic layer and washed with dilute HCl (30 ml). Separated the organic layer and distilled out ethyl acetate. To the residue, charged a solution of NaOH (1.53 g) in DM water (24 ml). Heated the reaction mixture up to 70° C. and stirred for 60 min. The reaction mass was cooled at 25-30° C. and extracted by ethyl acetate (36 ml). Separated the layers and aqueous layer was extracted by ethyl acetate (12 ml). Combined both organic layers and dried over anhydrous sodium sulphate and distilled out ethyl acetate to obtained 1.8 g of (1R)-1-(3-Methoxy-phenyl) ethanol (Yield: 92.78%, HPLC: 99.90%, Chiral by HPLC: 95.67% (R-isomer).

Example-18: Preparation of Pthalic Acid mono-[1-(3-methoxy-phenyl)-ethyl]ester (R)-(+)-1-Phenyl-propylamine Salt To a 500 ml RB flask, DM water (140 ml) and Phthalic acid mono-[1-(3-methoxy-phenyl)-ethyl]ester (20 g) were added. To the above reaction mixture a solution of KOH (2.24 g) in DM water (40 ml) was added drop wise at 65-70° C. To the above reaction mixture, (R)-(+)-1-phenylpropyl amine (6.27 g) was added drop wise at 65-70° C. Stirred the reaction mass for 60 min at 65-70° C., cooled the reaction mixture at 25-30° C. and stirred for 60 min. Filter the solid, washed with DM water (60 ml) and dried in vacuum oven at 50° C. to obtained 4.5 g of Phthalic acid mono-[1-(3-methoxy-phenyl)-ethyl] ester (R)-(+)-1-Phenylpropylamine salt (Yield: 15.5%, HPLC: 99.97%, Chiral Purity by HPLC: 95.77% (R-isomer).

1H NMR (400 MHz, DMSO): δ0.69-0.73 (t, 3H), δ 1.51-1.53 (d, 3H), δ 1.72-1.77 (m, 1H), δ 1.90-1.95 (m, 1H),

δ 3.75 (s, 3H), δ 3.69-4.00 (q, 1H), δ 5.88-5.93 (q, 1H), δ 6.83-6.85 (m, 1H), δ 6.98-7.00 (m, 2H), δ7.24-7.46 (m, 9H), δ8.19, (sb, 2H).

Example-19: Preparation of (1R)-1-(3-Methoxy-phenyl) ethanol

To a 250 ml RB flask, ethyl acetate (70 ml), Phthalic acid mono-[1-(3-methoxy-phenyl)-ethyl] ester (R)-(+)-1-Phenylpropylamine salt (10 g) and dilute HCl solution (100 ml) were added and stirred for 30 min. Layers were separated, organic layer washed with dilute HCl (50 ml). Separated the organic layer and distilled out ethyl acetate to obtain residue. To the residue, a solution of NaOH (2.75 g) in DM water (40 ml) was added. Heated the reaction mixture up to 70° C. and stirred for 60 min. The reaction mass cooled at 25-30° C. and extracted by ethyl acetate (60 ml). Layers were separated and aqueous layer was extracted by ethyl acetate (20 ml). Combined both organic layers, dried over sodium sulphate and distilled out ethyl acetate to obtained 3.45 g of (1R)-1-(3-Methoxy-phenyl) ethanol (Yield: 98.57%, HPLC: 99.96%, Chiral by HPLC: 98.50% (R-isomer).

1H NMR (400 MHz, DMSO): δ 1.31-1.32 (d, 3H), δ 3.74 (s, 3H), δ 4.66-4.72 (q, 1H), δ 5.17 (s, 1H), δ 6.76-6.78 (m, 1H), δ 6.89-6.92 (m, 2H), δ 7.19-7.23 (t, 1H)

Example-20: Preparation of Phthalic Acid mono-{1-[3-(ethyl-methyl-carbamoyloxy)-phenyl]-ethyl} ester (R)-(+)-1-Phenylpropylamine Salt To a 100 ml. RB flask, MTBE (50 ml), Phthalic acid mono-{1-[3-(ethyl-methyl-carbamoyloxy)-phenyl]-ethyl} ester (5 g) were added and heated the reaction mixture at 60-65° C. (R)-(+)-1-Phenylpropylamine (1.09 g) was added to the reaction mixture and stirred for 1 hour. Cooled the reaction mass to room temperature & stirred for 2 hours. Filtered the solid & dried to obtained 2.2 g of crude material. The crude material was stirred in MTBE (25 ml) at 60-65° C. for 1 hour. Gradually cooled to room temperature and stirred for 30 min, filtered the solid and washed with MTBE (7 ml). Dried the solid at 50-55° C. to obtained 1.81 g of Phthalic acid mono-{1-[3-(ethyl-methyl-carbamoyloxy)-phenyl]-ethyl} ester, (R)-(+)-1-Phenylpropylamine salt (Yield: 53%, HPLC: 99.61%, Chiral by HPLC: 98.30%).

1H NMR (400 MHz, CDCl$_3$): δ 0.68-0.71 (t, 3H), δ 1.16-1.22 (m, 3H), δ 1.55-1.56 (d, 3H), δ 1.86 (m, 2H), δ 2.96-3.04 (d, 3H, J=32 Hz), δ 3.37-3.45 (m, 2H), δ 3.38 (q, 1H), δ 5.79 (s, broad, 3H, D$_2$O Exchange), δ6.00-6.01 (d, 1H), δ 6.94-7.08 (m, 1H), δ7.11-7.24 (m, 1H), δ7.27-7.37 (m, 7H), δ7.38-7.43 (m, 2H), δ7.55-7.57 (d, 1H), δ7.64-7.65 (d, 1H).

Example-21: Preparation of (1R)-Ethyl-methyl-carbamic Acid 3-(1-hydroxy-ethyl)-phenyl ester To a 100 ml RB flask, ethyl acetate (18 ml), Phthalic acid mono-{1-[3-(ethyl-methyl-carbamoyloxy)-phenyl]-ethyl} ester, (R)-(+)-1-Phenylpropylamine salt (1.8 g) and dilute HCl solution (18 ml) were added stirred for 30 min. The organic layer separated and washed with dilute HCl (9 ml). The organic layer separated and distilled out ethyl acetate to obtain residue. To the residue, charged solution of NaOH (0.426 g) in DM water (7.2 ml). The reaction mixture heated up to 70° C. and stirred for 60 min. The reaction mass cooled at 25-30° C., extracted with ethyl acetate (11 ml), separated the layers and again aqueous layer extracted with ethyl acetate (4 ml). Combined both organic layers, dried over sodium sulphate and distilled out ethyl acetate to obtained 0.75 g of (1R)-Ethyl-methyl-carbamic acid 3-(1-hydroxy-ethyl)-phenyl ester (Yield: 95%, HPLC: 91.72%, Chiral by HPLC: 93.01% (R-isomer).

We claim:

1. A process for the preparation of compound of formula (V)

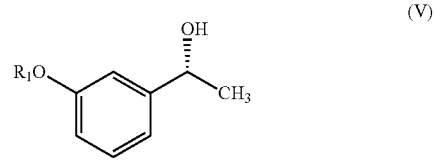

(V)

wherein R$_1$ represent C$_1$-C$_3$ alkyl or

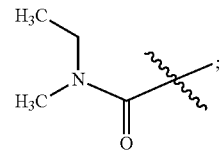

;

comprising the steps of:

a) reacting a compound of formula (II) with phthalic anhydride to obtain a compound of formula (III);

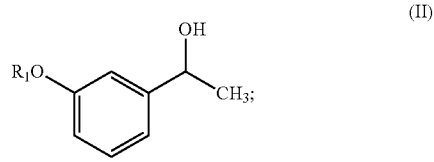

(II)

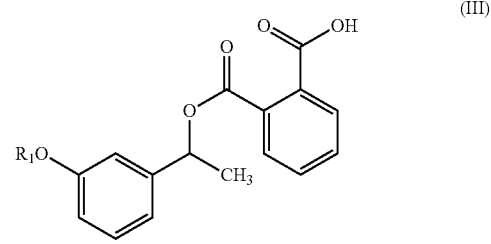

(III)

b) reacting the compound of formula (III) with a chiral resolving agent of formula (VI) to obtain a compound of formula (IV);

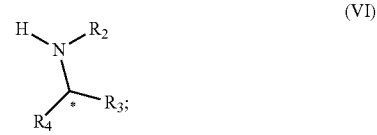

(VI)

-continued

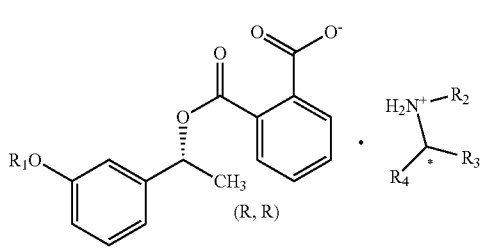

wherein * is a stereogenic center; $R_2$, $R_3$ and $R_4$ are selected from hydrogen, $C_{1-4}$ alkyl, $C_{6-10}$ aryl and $C_{7-12}$ alkylaryl, wherein $R_3$ and $R_4$ are different; and c) desaltification of the compound of formula (IV) followed by ester hydrolysis to obtain formula (V).

2. The process according to claim 1, wherein $R_2$, $R_3$ and $R_4$ are selected from hydrogen, $C_{1-4}$ alkyl, $C_{6-10}$ aryl and $C_{7-12}$ alkylaryl which are substituted with one or more methyl or methoxy.

3. The process according to claim 1, wherein the chiral resolving agent of formula (VI) is selected from 1-phenylethylamine, 1-Phenylpropylamine, α-Methyl-1-naphthalenemethylamine, N-benzyl-1-phenylethylamine, N,N-bis[α-methyl benzyl]amine, 1-(3-methoxyphenyl)ethylamine, 1-(3,4-dimethoxy-phenyl)ethyl amine, α-phenyl-β-(p-tolyl) ethylamine and 1-methyl-3-phenylpropylamine.

4. The process according to claim 1, wherein the chiral resolving agent of formula (VI) is (R)-1-phenylethylamine, (R)-(+)-1-Phenylpropylamine and (R)-(+)-α-Methyl-1-naphthalenemethylamine.

5. A compound of formula (III) and its salts

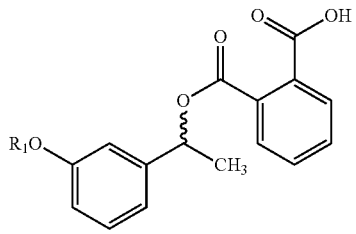

wherein $R_1$ wherein $R_1$ represent $C_1$-$C_3$ alkyl or

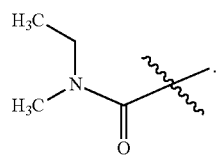 [SMILES: *C(=O)N(C)CC]

6. The compound of claim 5, wherein the compound is

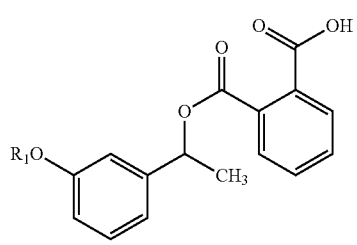

wherein $R_1$ wherein $R_1$ represent $C_1$-$C_3$ alkyl or

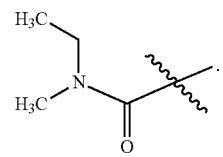 [SMILES: *C(=O)N(C)CC]

7. The compound of claim 5, wherein the compound is

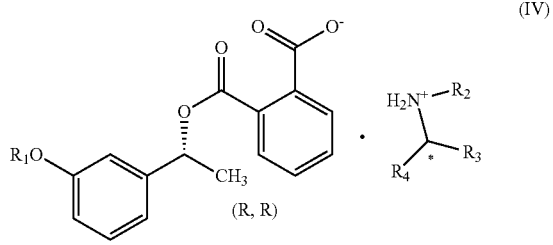

wherein $R_1$ represent $C_1$-$C_3$ alkyl or

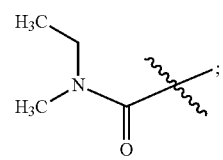 [SMILES: *C(=O)N(C)CC]

* is a stereogenic center;
$R_2$, $R_3$ and $R_4$ are selected from hydrogen, $C_{1-4}$ alkyl, $C_{6-10}$ aryl and $C_{7-12}$ alkylaryl, which are optionally substituted with one or more methyl or methoxy, wherein $R_3$ and $R_4$ are different.

8. A process for the preparation of Rivastigmine of formula (I) or its pharmaceutically acceptable salts comprising the steps of:
   a) reacting a compound of formula (II) with phthalic anhydride to obtain a compound of formula (III);
   b) reacting the compound of formula (III) with a chiral resolving agent of formula (VI) to obtain a compound of formula (IV);
   desaltification of the compound of formula (IV) followed by ester hydrolysis to obtain formula (V);
   wherein $R_1$ of formula (V) is $C_1$-$C_3$ alkyl then the compound of formula (V) under goes amidation and converting the methoxy on phenyl to hydroxyl before final conversion to Rivastigmine of formula (I) or its pharmaceutical acceptable salt; or $R_1$ of formula (V) is
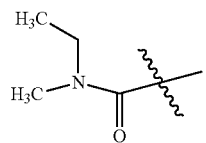 [SMILES: *C(=O)N(C)CC]
then compound of formula (V) directly under goes amidation to obtain Rivastigmine of formula (I) or its pharmaceutical acceptable salt.
* * * * *